(12) United States Patent
Fadler

(10) Patent No.: US 8,378,325 B2
(45) Date of Patent: Feb. 19, 2013

(54) MEDICAL DEVICE HAVING A COLLISION PROTECTION APPARATUS

(75) Inventor: Franz Fadler, Hetzles (DE)

(73) Assignee: Siemens Aktiengesellschaft, München (DE)

( * ) Notice: Subject to any disclaimer, the term of this patent is extended or adjusted under 35 U.S.C. 154(b) by 196 days.

(21) Appl. No.: 12/830,009

(22) Filed: Jul. 2, 2010

(65) Prior Publication Data
US 2011/0006230 A1 Jan. 13, 2011

(30) Foreign Application Priority Data

Jul. 9, 2009 (DE) .......................... 10 2009 032 431

(51) Int. Cl.
  A61B 6/04 (2006.01)
  A61N 5/00 (2006.01)
  A61N 5/01 (2006.01)

(52) U.S. Cl. .......... 250/505.1; 250/522.1; 5/601; 5/611; 378/20; 378/65; 378/195

(58) Field of Classification Search ............... 250/505.1, 250/522.1; 5/601, 611; 378/20, 65, 195
See application file for complete search history.

(56) References Cited

U.S. PATENT DOCUMENTS

| 7,492,858 B2* | 2/2009 | Partain et al. ............... 378/37 |
| 7,640,607 B2* | 1/2010 | Guertin et al. ............... 5/601 |
| 7,860,550 B2* | 12/2010 | Saracen et al. ............... 600/410 |
| 2007/0003010 A1 | 1/2007 | Guertin et al. |
| 2007/0003021 A1 | 1/2007 | Guertin et al. |
| 2008/0273659 A1 | 11/2008 | Guertin et al. |
| 2011/0007867 A1* | 1/2011 | Fadler ............... 378/20 |
| 2011/0085640 A1* | 4/2011 | Fadler ............... 378/62 |

FOREIGN PATENT DOCUMENTS

WO WO 2007018646 A1 2/2007

* cited by examiner

*Primary Examiner* — Nikita Wells

(74) *Attorney, Agent, or Firm* — Lempia Summerfield Katz LLC

(57) ABSTRACT

A medical device includes a moving gantry, on which a radiation source is arranged, and a collision-protection apparatus for preventing a patient from colliding with the moving gantry. The gantry is operable to be moved around a patient-positioning apparatus. The collision-protection apparatus can be configured as a mechanical collision-protection apparatus that is operable to be positioned between the patient and the moving gantry. The collision-protection apparatus can also be configured as a collision-monitoring apparatus that detects the crossing of a predefined volume by an object, the collision-monitoring apparatus having a control apparatus that controls the motion of the gantry as a function of whether a crossing of the volume has or has not been detected.

20 Claims, 5 Drawing Sheets

MEDICAL DEVICE HAVING A COLLISION PROTECTION APPARATUS

This application claims the benefit of DE 10 2009 032 431.3 filed on Jul. 9, 2009, which is hereby incorporated by reference.

BACKGROUND

The present embodiments relate to a medical device having a moving gantry.

Medical devices that have a moving gantry are found in the field of radiation therapy, with the therapy source being arranged on the gantry. Medical devices of such type often have projecting parts that are moved around a patient in order, for example, to direct the therapy beam onto the patient from different directions.

SUMMARY AND DESCRIPTION

The present embodiments may obviate one or more of the drawbacks or limitations in the related art. For example, in one embodiment, a medical device that combines gantry motion with a high degree of patient safety is provided.

The medical device of the present embodiments (e.g., a radiation-therapy device) includes a moving gantry, on which a radiation source is arranged. The gantry is operable to be moved around a patient-positioning apparatus, with the medical device having a collision-protection apparatus for preventing a patient located on the patient-positioning apparatus from colliding with the moving gantry.

The medical device may be, for example, a radiation-therapy device having a moving gantry that has a projecting arm. An x-ray source such as, for example, a radiation-therapy source that directs an x-ray or a therapy beam onto the patient, may be secured to the projecting arm. The collision-protection apparatus enables the medical device to be operated more safely. Harm to patients due a collision between the patient and the gantry's rotating collision points or edges (e.g., a projecting arm) may be prevented. The moving gantry may be moved at faster speeds because of the use of the collision-protection apparatus. Consequently, the medical device may be operated more effectively and economically.

In one embodiment, the collision-protection apparatus is a mechanical collision-protection apparatus that may be positioned between the patient and moving gantry. The mechanical collision-protection apparatus may be moved out manually or motor-driven from a parked position. The mechanical collision-protection apparatus prevents the limit of the volume within which the patient is positioned from being accidentally crossed by the rotating gantry. The mechanical collision protection apparatus thus forms a mechanical separation between the patient's space and rotatable gantry components. The mechanical collision protection apparatus has the advantage of being very easy to check (e.g., by looking) whether the protection has or has not been activated.

In one embodiment, a control apparatus may control moving out of the mechanical collision-protection apparatus, such that the mechanical collision-protection apparatus is moved out when a speed of the gantry exceeds a threshold. For example, the control apparatus may move the mechanical collision protection apparatus out whenever the rotational speed of the gantry exceeds 7°/s. The mechanical collision protection apparatus, which a patient may find constricting, is not always present (e.g., when speeds are involved at which a collision poses no or little danger).

In one embodiment, the control apparatus may allow gantry movements at a speed exceeding a threshold only if the collision protection apparatus has been brought into position. For example, speeds less than 7°/s are allowed with no mechanical collision protection, and speeds exceeding 7°/s are not allowed unless the mechanical collision-protection apparatus has been moved out. Accordingly, the mechanical collision protection apparatus is activated for movements that are potentially dangerous for a patient. In one embodiment, the control apparatus controls moving out of the mechanical collision-protection apparatus such that the mechanical collision-protection apparatus is moved out automatically when a speed of the gantry exceeds the threshold.

In one embodiment, the mechanical collision-protection apparatus may have a folding bellows or be configured as a folding bellows shaped as, for example, a complete pipe or a half pipe.

In one embodiment, the mechanical collision-protection apparatus may include a section (e.g. a section that surrounds the patient when the mechanical collision-protection apparatus has been moved out) with a transparent material. Optical transparency may produce a more pleasant sensation for claustrophobic patients, for example, because the optical transparency may be less constricting. The patient may also be observed through the mechanical collision-protection apparatus. The functionality of the medical device is minimally affected by transparency for x-rays or therapeutic radiation.

In one embodiment, the folding bellows may be secured to a gantry area formed by, for example, a gantry covering. The folding bellows may be secured to an area of the patient table facing the gantry. The gantry area may have a depression, into which the bellows may be retracted in a folded condition. There are no projecting parts against which users may bump themselves when the bellows is in the folded condition.

In one embodiment, the gantry has a tubular central opening, into which a patient may be moved using the patient-positioning apparatus. The mechanical collision protection apparatus is arranged on the gantry such that an extension to the tubular central opening is produced when the mechanical collision protection apparatus is brought between the patient and gantry. An effective collision protection may be provided in a simple manner in the case, for example, of medical devices having a projecting arm that moves around the axis of the tubular opening.

In another embodiment, the collision-protection apparatus may be configured as a collision-monitoring apparatus. The crossing of a predefined volume by an object may be detected using the collision-monitoring apparatus, and the collision-monitoring apparatus has a control apparatus that controls the motion of the gantry as a function of whether a crossing of the volume has or has not been detected. A collision-monitoring apparatus of such type is based not on mechanical components but may be based on sensors that emit optical, electromagnetic, and/or acoustic waves and detect crossing of the volume using a wave reflection. The sensors may be reflection/distance sensors. The advantage is that no mechanically projecting components are used. The collision-monitoring apparatus may be quickly activated, in contrast to mechanical collision-protection apparatuses that take a certain amount of time to engage. Claustrophobic patients may not feel constricted. The patient cannot collide with the collision-protection apparatus, as is possible with mechanical collision-protection apparatuses.

In one embodiment, the collision-monitoring apparatus may include a light curtain that extends around the longitudinal direction of a patient table and emanates from a plurality of sensors arranged in a circle, for example, in a gantry area (e.g., on a covering of the gantry and/or in a gantry area facing the patient-positioning apparatus). For the gantry that has a tubular central opening, the sensors, from which the light curtain emanates, may be arranged, for example, on a gantry front encircling the tubular central opening.

A virtual monitoring cylinder is formed around the patient. The sensors may monitor the location and/or distance of relevant collision points.

In one embodiment, the sensors may be operated in an operating mode where one part of the plurality of sensors has been activated. Activating may, for example, be set as a function of a turning direction and angular position of the gantry. Activating as a function of the turning direction and angular position of the gantry enables the sensors to be operated economically and avoids erroneous detecting in regions in which no collisions take place because of the angular position, turning direction, and geometry of the gantry.

In one embodiment, the collision-monitoring apparatus may be formed by a moving laser scanner, with the laser scanner proceeding from a point and scanning the predefined volume to be monitored by moving an emitted laser bundle. The emitted laser bundle may be fan-shaped, for example, and scan the predefined volume through a back-and-forth or rotational movement. The laser bundle may register the table-top, accessory, and/or patient volume. If there is any overlapping between one of the table-top, the accessory, and/or the patient volume and the space for moving the gantry, the speed of the gantry may be reduced, or the gantry may be stopped.

The scanned volume may be set or selected as a function of a turning direction and angular position of the gantry. Thus, the volume in which a collision may occur may always be monitored, while spatial regions in which a collision with the patient may not occur (e.g., owing to the geometry of the medical device) are excluded from monitoring. Incorrect controlling of the gantry is avoided.

For a gantry that has a tubular central opening, the emitted laser bundle may be arranged such that the emitted laser bundle passes through the central opening. A volume having the nature of a cylinder around the patient table may be scanned advantageously.

A control apparatus may control the motion of the gantry, for example, as a function of an angular position and/or distance of a measured crossing of the predefined volume. The motion may, for example, be slowed down whenever the predefined volume is crossed in a spatial region where a collision with, for example, a projecting arm of the gantry may occur. If it is determined that the predefined volume is crossed in a spatial region, which owing to the geometry of the medical device, that is distant from possible collision points, the motion of the gantry may nonetheless be continued.

DETAILED DESCRIPTION OF THE DRAWINGS

Figure 1:
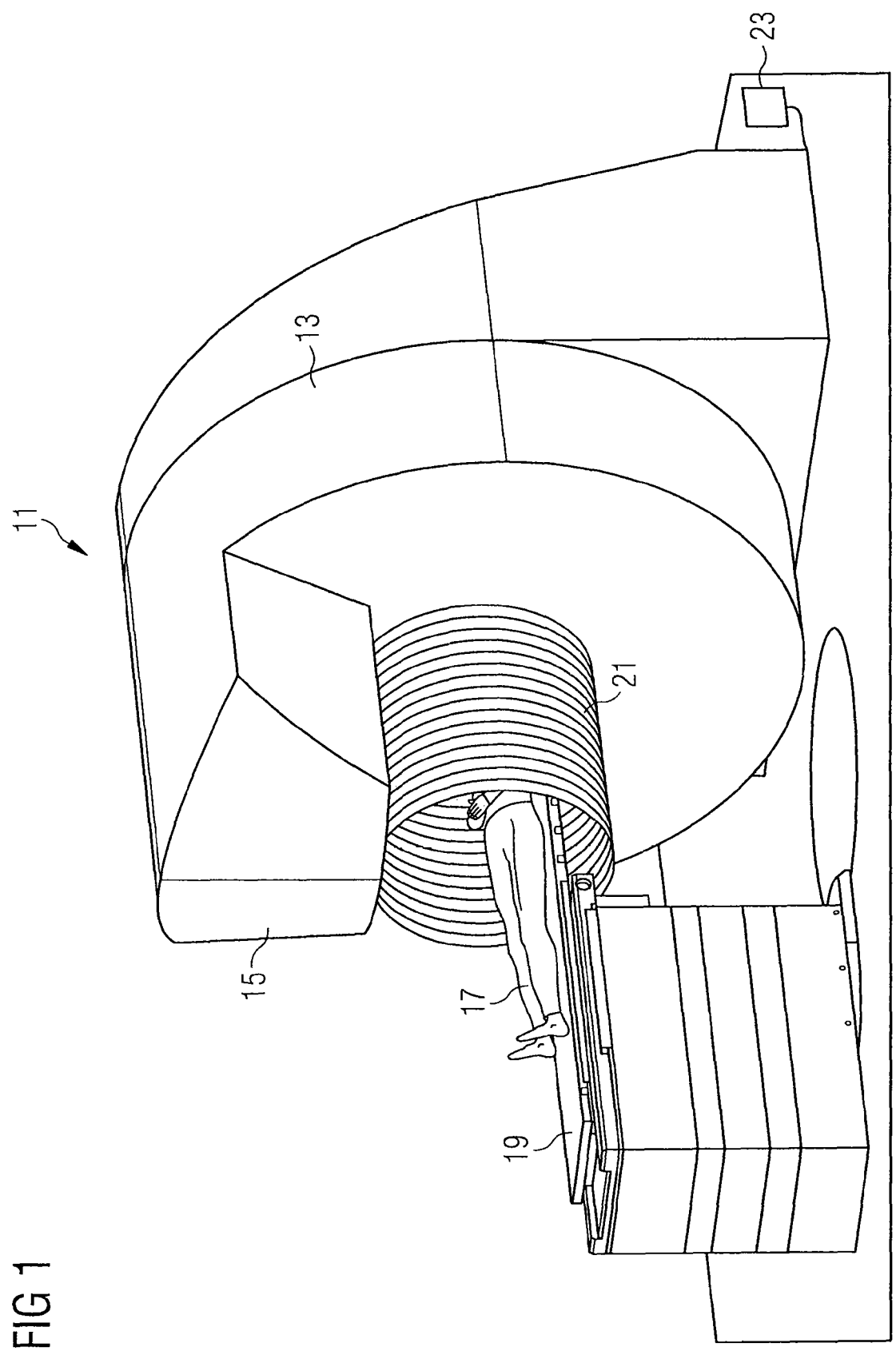
FIG. 1 shows one embodiment of a radiation-therapy device having mechanical collision protection.

FIG. 1 shows one embodiment of a radiation-therapy device 11 that has a mechanical collision-protection apparatus. The radiation-therapy device 11 shown in FIG. 1 is constructed as an o-shaped gantry 13 with a projecting arm 15 secured on the gantry 13. The projecting arm 15 includes parts of an accelerator apparatus as well as a beam-application apparatus (e.g., a collimator) so that therapeutic radiation may be directed onto a patient 17 from the projecting arm 15. A patient table 19 that is operable to move translationally and rotationally may orient the patient 17 relative to the therapy beam. The patient 17 may also be moved partially into the central opening (e.g., the tubular opening) of the o-shaped gantry 13.

The gantry 13 may be rotated around a horizontal central axis so that the therapy beam may be directed onto the patient 17 from different spatial directions. A risk exists that the patient 17 will collide with the projecting arm 15 or with other protruding parts (not shown) that are moved through the motion of the gantry 13. To prevent the collision, a bellows 21 may be moved out, as shown in FIG. 1, such that a mechanical barrier is established between the patient 17 and moving parts of the gantry 13. The bellows 21 shown in the embodiment of FIG. 1 is configured as a complete pipe constituting an extension of the tubular opening of the gantry 13. In one embodiment, the mechanical bellows 21 includes a transparent material to be able to observe (not shown) the patient 17 through the bellows 21.

A control apparatus 23 (shown schematically) controls the movement of the bellows 21, such that the bellows 21 is moved out as soon as the gantry 13 is to be turned at speeds exceeding a predefined threshold. Additionally or alternatively, the control apparatus 23 prevents the gantry 13 from turning at speeds exceeding the predefined threshold unless the bellows 21 has been moved out.

Figure 2:
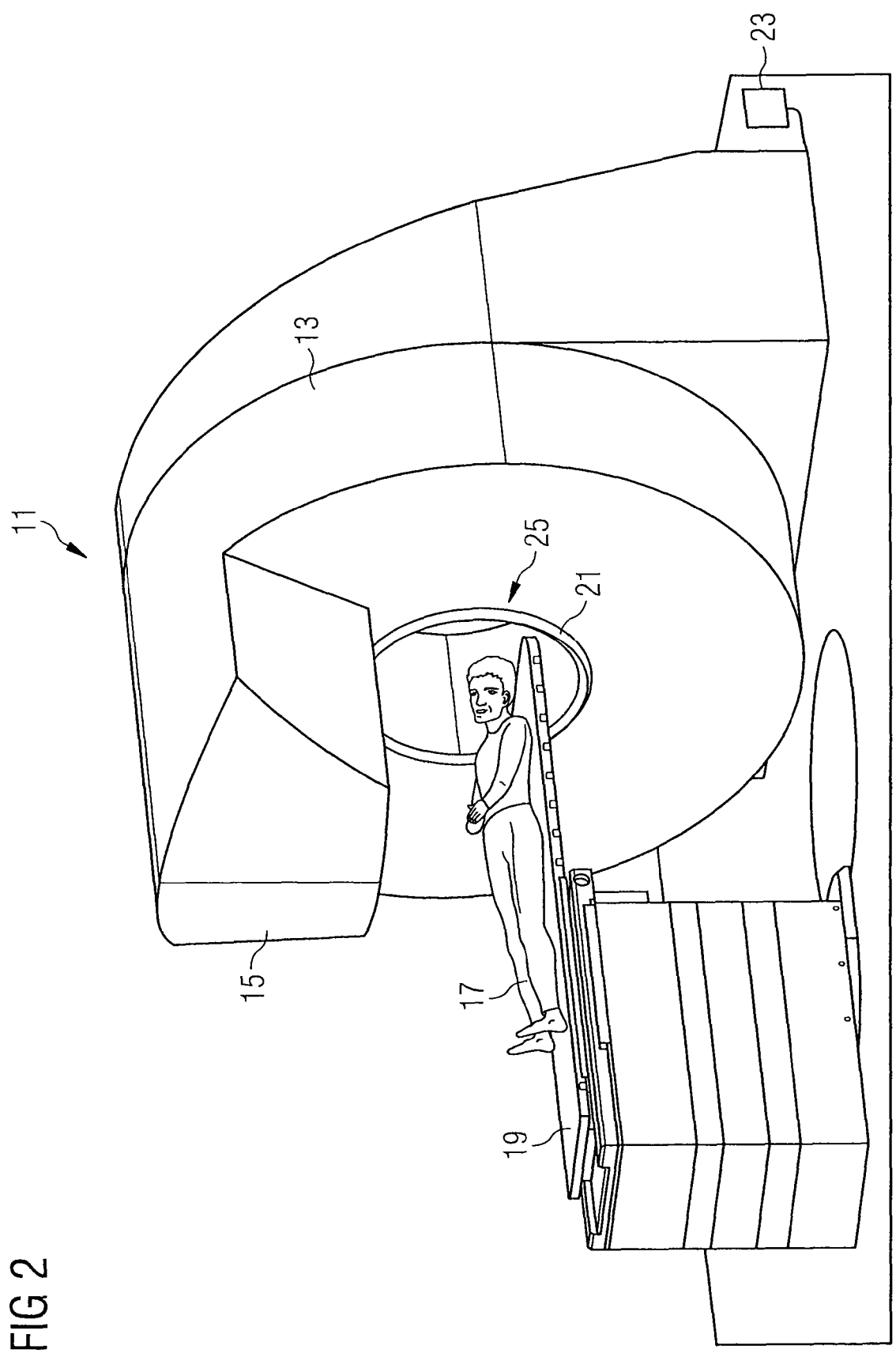
FIG. 2 shows one embodiment of the radiation-therapy device of FIG. 1 having retracted collision protection.

FIG. 2 shows one embodiment of the radiation-therapy device 11 shown in FIG. 1 with the bellows 21 in a retracted condition. A covering of the gantry 13 includes a recess 25, into which the bellows 21 may be folded away in the retracted condition. The retracted bellows 21 will, as a result, lie flush with the covering of the gantry 13. That retracted condition of the bellows 21 may be assumed, for example, for initially positioning the patient 17 or if the gantry 13 is moved only at below-threshold speeds.

Figure 3:
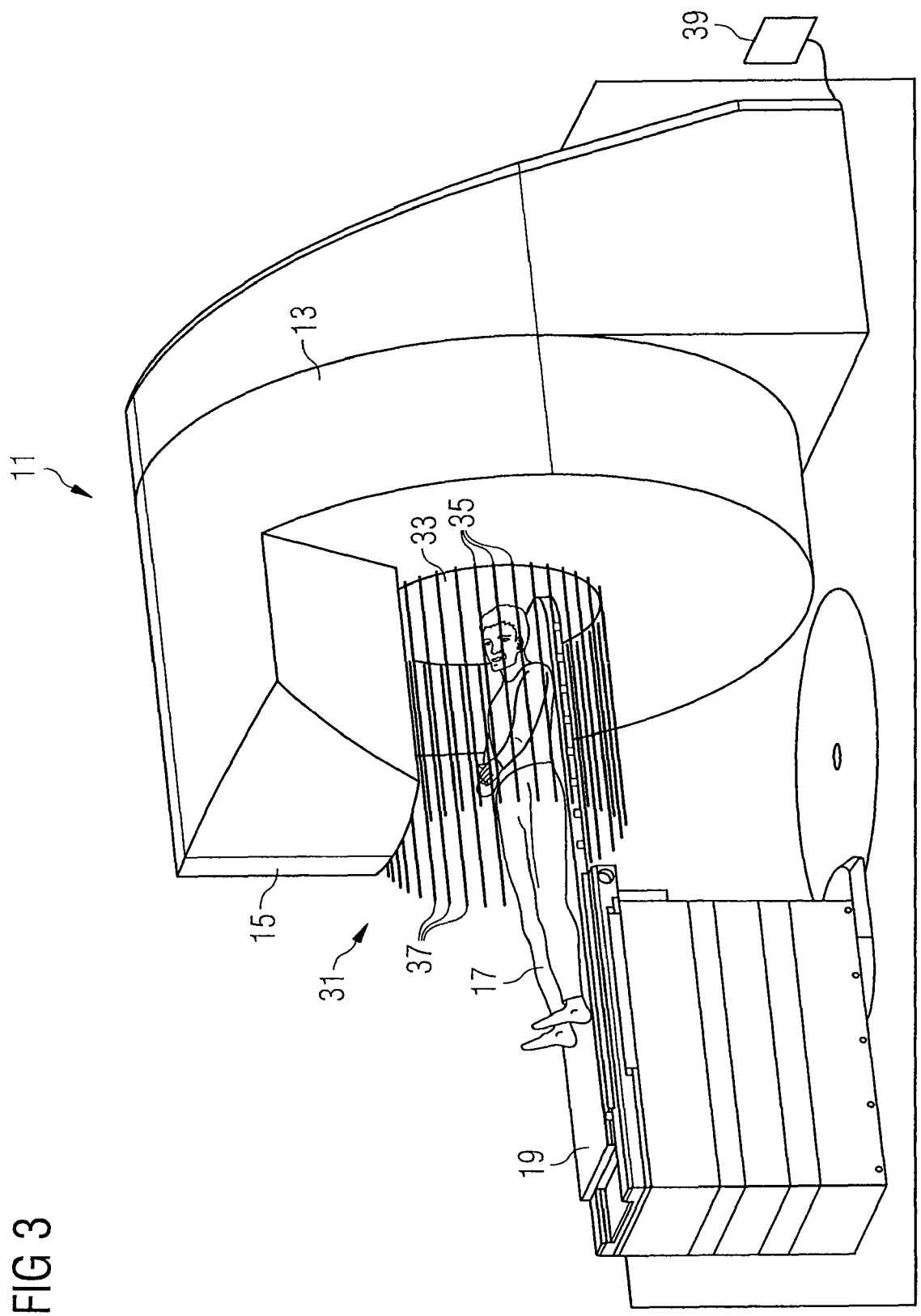
FIG. 3 shows one embodiment of a radiation-therapy device having a collision-monitoring apparatus.

FIG. 3 shows one embodiment of a collision-protection apparatus configured as a collision-monitoring apparatus 31. A row of reflection/distance sensors 35 is arranged around the tubular opening 33 of the o-shaped gantry 13 for collision-monitoring. A light beam 37 (e.g., a light barrier 37) emanates from each of the reflection/distance sensors 35. The reflection/distance sensors 35 are operable to detect an interruption of the light barrier 37 if the interruption occurs within a specific range. The light barrier 37 simulates as if the light barrier was a light curtain and thus a "virtual" mechanical bellows.

As soon as a crossing of the light barrier 37 is determined, the reflection/distance sensors 35 supply a signal to a control apparatus 39 that controls the motion of the gantry 13. The control apparatus 39 may control the motion of the gantry 13 as a function of the position of the projecting arm 15, of the turning direction of the gantry 13, of the turning speed of the gantry 13, and/or of the place at which crossing of the light barrier 37 was determined. For example, the gantry motion may be slowed down or halted.

Figure 4:
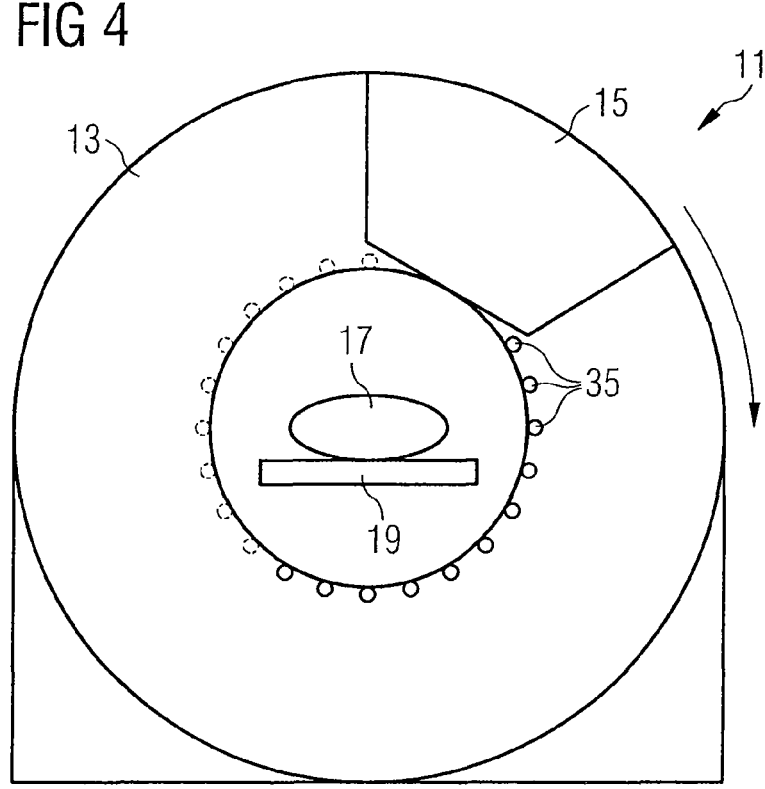
FIG. 4 and FIG. 5 each show a front view of one embodiment of a radiation-therapy device.
Figure 5:
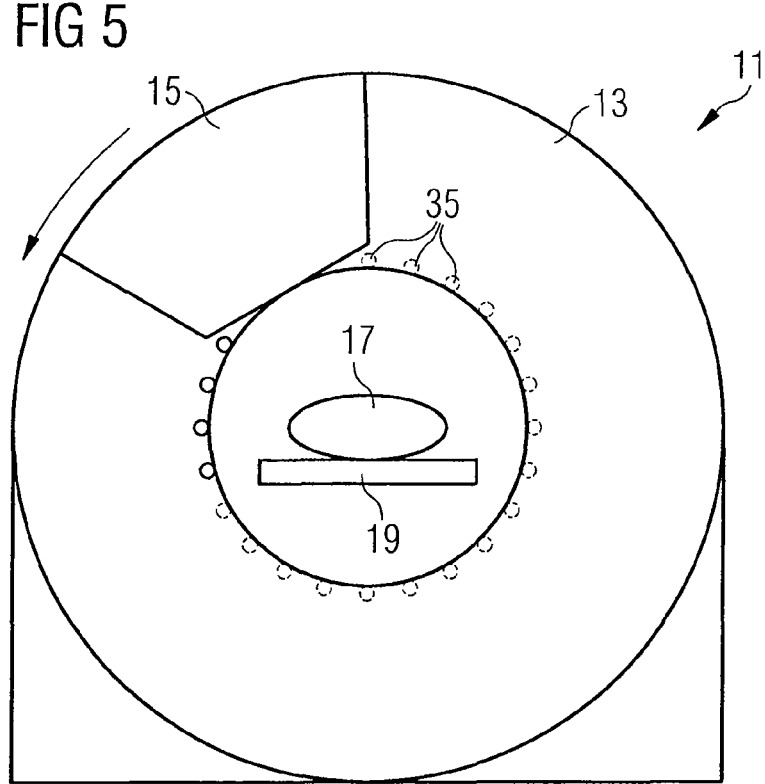

FIG. 4 and FIG. 5 are both front views of one embodiment of the gantry 13 shown in FIG. 3. FIGS. 4 and 5 show one embodiment of the collision monitoring apparatus 31 shown in FIG. 3, where a portion of the reflection/distance sensors 35 is activated (e.g., as a function of how fast and in what direction the gantry 13 is turning and where a possible collision with the patient 17 may be expected).

The reflection/distance sensors 35, when activated, may also detect breaking of the light beam 37 emitted by reflection/distance sensors 35. Activated sensors 35 are shown in FIGS. 4 and 5 using an unbroken circle, in contrast to those shown as dotted circles that identify the inactive condition.

In the example shown in FIG. 4, the gantry 13 turns clockwise at a relatively high speed so that the sensors 35 in a semicircle located in front of the projecting arm 15 in the turning direction are activated for collision monitoring. Activation of the sensors 35 changes as the gantry 13 turns.

In FIG. 5, the gantry 13 turns counter-clockwise. Because the turning speed of the gantry 13 is slower, the sensors 35 of a quarter circle are activated, specifically the sensors 15 located in front of the projecting arm 15 in the counter-clockwise turning direction. Detecting that is not relevant to a risk of collision is avoided, and the region in which a collision is possible or may be expected is be controlled.

Figure 6:
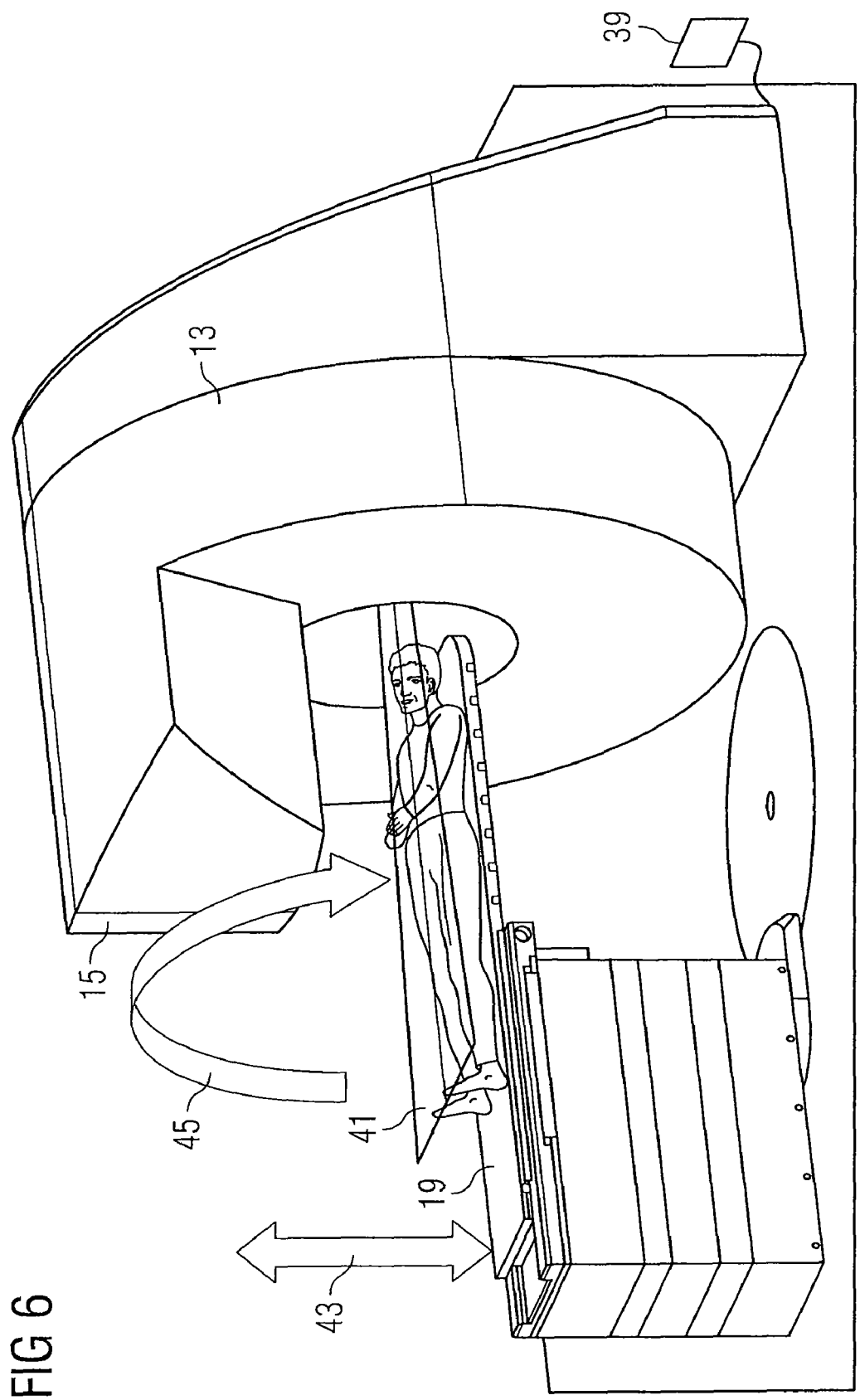
FIG. 6 shows one embodiment of a radiation-therapy device with one embodiment of a collision-monitoring apparatus.

FIG. 6 shows one embodiment of a radiation-therapy device in which the volume that the patient 17 is positioned in is scanned using a laser fan 41 proceeding from a point. The laser fan 41 projects through the tubular opening 33 of the gantry 13 in the example shown in FIG. 6. The patient volume is monitored by the laser fan 41 moving and thereby scanning the patient volume. The movement may be, for example, an up-and-down movement, indicated by the double arrow 43, or a rotational movement, shown by the bent arrow 45. The movement of the gantry 13 may be stopped as soon as it is determined that the volume has been crossed by, for example, an arm of the patient 17. As discussed above, the sensitive volume that is checked by the laser fan 41 in terms of being crossed over may be set, for example, as a function of the turning direction and/or turning speed of the gantry 13.

The embodiments presented above were described on the basis of an o-shaped gantry 13. The embodiments presented above also apply to other gantry configurations such as, for example, an L-shaped gantry having a projecting arm. The collision-protection apparatus may, in the case of the L-shaped gantry, be arranged on the vertical area of the gantry pointing toward the patient-positioning apparatus.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical device comprising:
a moving gantry operable to be moved around a patient-positioning apparatus;
a radiation source arranged on the moving gantry; and
a collision-protection apparatus for preventing a patient from colliding with the moving gantry,
wherein the collision-protection apparatus comprises a collision-monitoring apparatus that is operable to detect an object crossing a predefined volume, and
wherein the collision-monitoring apparatus comprises a control apparatus configured to control the motion of the moving gantry as a function of whether the object has or has not been detected crossing the predefined volume.

2. The medical device as claimed in claim 1, wherein the collision-protection apparatus is a mechanical collision-protection apparatus that is operable to be positioned between the patient and the moving gantry.

3. The medical device as claimed in claim 2, wherein the control apparatus is configured to control the positioning of the mechanical collision-protection apparatus such that the mechanical collision-protection apparatus is positioned when a speed of the gantry exceeds a threshold.

4. The medical device as claimed in claim 3, wherein the medical device is configured such that speeds of the moving gantry cannot exceed a threshold unless the mechanical collision-protection apparatus is positioned between the patient and the moving gantry.

5. The medical device as claimed in claim 2, wherein the medical device is configured such that speeds of the moving gantry cannot exceed a threshold unless the mechanical collision-protection apparatus is positioned between the patient and the moving gantry.

6. The medical device as claimed in claim 2, wherein the mechanical collision-protection apparatus comprises a folding bellows configured as a folding partial or complete pipe.

7. The medical device as claimed in claim 6, wherein the folding bellows is secured to a gantry area.

8. The medical device as claimed in claim 7, wherein the gantry area comprises a depression, into which the folding bellows is retracted in a folded condition.

9. The medical device as claimed in claim 2, wherein the mechanical collision-protection apparatus comprises a transparent material.

10. The medical device as claimed in claim 2, wherein the moving gantry comprises a tubular central opening, and
wherein an extension to the tubular central opening is produced by moving the mechanical collision-protection apparatus out.

11. The medical device as claimed in claim 1, wherein the collision-monitoring apparatus comprises a plurality of sensors arranged in a gantry area of the medical device, and
wherein a light curtain that extends around the longitudinal direction of a patient-positioning apparatus emanates from the plurality of sensors.

12. The medical device as claimed in claim 11, wherein only one part of the plurality of sensors is operable to be activated in one operating mode as a function of a turning direction and angular position of the moving gantry.

13. The medical device as claimed in claim 11, wherein the moving gantry comprises a tubular central opening, and
wherein the plurality of sensors are arranged on a gantry front encircling the tubular central opening.

14. The medical device as claimed in claim 1, wherein the collision-protection apparatus comprises a moving laser scanner, the moving laser scanner operable to proceed from a point and scan the predefined volume by moving a laser bundle emitted from the moving laser scanner.

15. The medical device as claimed in claim 14, wherein the emitted laser bundle is fan-shaped.

16. The medical device as claimed in claim 14, wherein the laser scanner is operable to scan the predefined volume using the emitted laser bundle through a back-and-forth movement or a rotational movement.

17. The medical device as claimed in claim 14, wherein the moving gantry comprises a tubular central opening, and
wherein the emitted laser bundle passes through the central opening.

18. The medical device as claimed in claim 14, wherein the scanned predefined volume is selected as a function of a turning direction and angular position of the moving gantry.

19. The medical device as claimed in claim 1, wherein the control apparatus is operable to control the motion of the moving gantry as a function of an angular position, a distance of a measured crossing of the predefined volume or the angular position and the distance of the measured crossing of the predefined volume.

20. A medical device comprising:

a moving gantry operable to be moved around a patient-positioning apparatus;

a radiation source arranged on the moving gantry; and a collision-protection apparatus for preventing a patient from colliding with the moving gantry, wherein the collision-protection apparatus comprises a mechanical collision-protection apparatus that is operable to be positioned between the patient and the moving gantry, and wherein a control apparatus of the collision-protection apparatus is configured to control the positioning of the mechanical collision-protection apparatus such that the mechanical collision-protection apparatus is moved into a position, in which the mechanical collision-protection apparatus establishes a mechanical barrier between the patient and the moving gantry, when a speed of the gantry exceeds a threshold.

\* \* \* \* \*